United States Patent [19]

Brown et al.

[11] Patent Number: 4,895,945

[45] Date of Patent: Jan. 23, 1990

[54] EPOXIDIZED CHLOROTRIAZINE COMPOUNDS

[75] Inventors: Sterling B. Brown, Schenectady; Richard C. Lowry, Clifton Park, both of N.Y.

[73] Assignee: General Electric Company, Schenectady, N.Y.

[21] Appl. No.: 144,901

[22] Filed: Jan. 19, 1988

[51] Int. Cl.$^4$ ............................................ C07D 251/26
[52] U.S. Cl. ..................................................... 544/218
[58] Field of Search ................................ 544/219, 218

[56] References Cited

U.S. PATENT DOCUMENTS

| | | | |
|---|---|---|---|
| 2,769,004 | 10/1956 | Huemer | 544/219 |
| 2,936,227 | 5/1960 | Gysin et al. | 544/219 |
| 3,053,799 | 9/1962 | D'Alelio | 544/219 |
| 3,156,690 | 11/1964 | Dexter et al. | 544/219 |

*Primary Examiner*—John M. Ford
*Attorney, Agent, or Firm*—William H. Pittman; James C. Davis, Jr.

[57] ABSTRACT

Epoxidized chlorotriazine compounds, useful to introduce one or more epoxide groups into nucleophile containing polymers, are prepared by reacting an epoxy alcohol with a cyanuric chloride or dichlorotriazine in the presence of base.

6 Claims, No Drawings

EPOXIDIZED CHLOROTRIAZINE COMPOUNDS

The invention relates to chloroepoxytriazines useful for introducing epoxy functional groups into nucleophilic polymers and to a method for making the substituted triazines.

There are a number of applications for functionalized nucleophilic polymers. One of the most important of these is copolymer formation by reaction of the functional group of said polymer with a second polymer. It is known that the resulting copolymer may serves as a compatibilizing agent to prevent polymer agglomeration in physical blends comprising relatively non-miscible polymers. It is also known that the mechanical and physical properties of nucleophilic polymers may be improved by copolymerization with a second polymer.

For example, polyphenylene ether is an extremely useful nucleophilic polymeric resin having excellent heat resistance, mechanical properties, electrical properties, hot water resistance, acid resistance, alkali resistance, self-extinguishing characteristics, and has found wide applications as an engineering thermoplastic material. However, improvements in melt viscosity, processibility, organic solvent resistance and impact resistance would provide a wider range of application for polyphenylene ether-containing resins.

A principal object of the present invention, therefore, is to provide chloroepoxytriazines which can be used to introduce an epoxy group into nucleophilic polymers such as polyphenylene ethers, polycarbonates, and the like.

A further object is to provide a method for preparing monofunctional and difunctional chloroepoxytriazines.

An object of this invention is to provide a method for making chlorotriazines having one or two epoxy-containing substituents.

Another object of the invention is to provide means for incorporating epoxide-containing compounds into a polymer.

Another object of the invention is to facilitate formation of copolymers of an epoxy functionalized polymer and another polymer capable of reacting with an epoxy group.

The chloroepoxytriazines of this invention have the formula

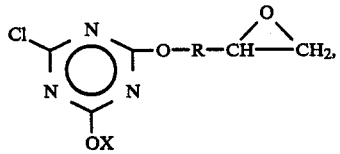

wherein -R- is a divalent hydrocarbon residue corresponding to alkyl and cycloalkyl groups, divalent mononuclear aromatic groups, aryl substituted divalent alkyl groups, and divalent heterocyclic groups and -X is an alkyl group, aromatic group, aryl substituted alkyl group, or

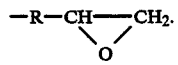

Preferred alkyl groups represented by -R- and -X include alkane residues having from 1 to about 18, and preferably from 1 to 6, carbon atoms in straight or branched chain configurations. Illustrative groups include methylene, ethylene, propylene, tetramethylene, decamethylene, 2-methyltrimethylene, 2,2-dimethyltrimethylene, 3-ethylpentamethylene, and the like.

Cycloalkyl or alicyclic residues include those containing from 4 to about 7 carbon atoms in cyclic chain such as cyclobutyl, cyclopentyl, methylcyclohexyl, cycloheptyl, and the like.

Aromatics include arylenes, such as phenylene and substituted phenylene, having from 6 to 12 carbon atoms in the aromatic nucleus, such as 1,4-phenylene, phenylphenylene, 4-methyl-1,2-phenylene, 2,3-naphthylene, 2,6-naphthylene, 7-methyl-2,6-naphthylene, and the like. These groups can be visualized as monovalent or divalent arylalkyl and alkaryl groups corresponding to benzyl, ethylphenyl, phenylpropyl, and the like.

Suitable divalent heterocyclic groups are those containing from 4 to about 7 atoms in the ring, including one or more nitrogen or oxygen atoms, such as divalent groups derived from pyridine, pyran, pyrrole, pyrimidine, and the like.

The chloroepoxytriazines of this invention can be prepared by reacting an epoxy alcohol of the formula:

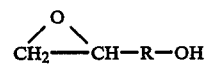

with a cyanuric chloride or dichlorotriazine of the formula:

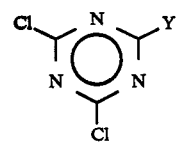

where R is a divalent hydrocarbon, as previously defined, and Y is chlorine or OX where X is an aromatic group, aryl substituted alkyl group, or an alkyl group.

Aromatics include arylenes such as phenylene and substituted phenylene having from 6 to 12 carbon atoms in the aromatic nucleus, such as 1,4-phenylene, phenylphenylene, 4-methyl-1,2-phenylene, 2,3-naphthylene, 2,6-naphthylene, 7-methyl-2,6-naphthylene, and the like. These groups can be visualized as monovalent arylalkyl and alkaryl groups corresponding to benzyl, ethylphenyl, phenylpropyl, and the like.

The alkoxy groups within the scope of the present invention have from 1 to about 18 carbons and are preferably a lower alkoxy group having from 1 to 6 carbons.

Suitable solvents for preparation of chloroepoxytriazines include water immiscible organic solvents for the reactants and reaction products, such as chloroform, toluene, dichlorobenzene, methylene chloride and the like.

The chlorodiepoxytriazines and alkoxy chloroepoxytriazines of this invention can be prepared by dissolving the epoxy alcohol and the cyanuric chloride or alkoxy substituted cyanuric chloride, i.e., alkoxy dichlorotriazine, in approximately stoichiometric amounts in a suitable water immiscible solvent. Generally, the reactants are present in combined amounts ranging from about 10 to about 60 weight percent, preferably 25 to 40 weight percent, based on the weight of total solution. Precise concentrations of reactants in solution is not narrowly critical, provided that the reactants are substantially all in solution The reaction which involves replacement of one or two chlorine atoms on the triazine ring is promoted by a base which is added to and admixed with the reactant solution in controlled amounts. Solid alkali or alkaline earth metal hydroxides, aqueous solutions of alkali or alkaline earth metal hydroxides, and strongly basic amines can be used. Sodium and potassium hydroxide are preferred. The addition of base is controlled in order to minimize self polymerization of the epoxy-containing anion formed by removal of the hydroxy hydrogen or proton from the alcohol. The anion then replaces one or two reactive chlorines on the triazine ring in order of reactivity within the stoichiometric limits imposed by the availability of the epoxy-carrying anion. Best results are obtained when the base is added slowly wth adequate mixing, allowing time for complete utilization of base in the formation of epoxy anion followed by reaction with chloro substituted triazine. High concentrations of anion in the presence of a base tend to promote polyether formation.

The reaction which can be interfacial or solution, depending on choice of base, is carried out at a temperature below the boiling point of the organic solvent or liquid phase. Generally, temperatures below about 10° C. are preferred with a temperature range of about 0° to 5° C. being most preferred.

When the selected base is a solid which is not soluble in the organic solvent, or an aqueous solution, chloroepoxytriazines are formed in the present invention by reaction of the alkoxide ion of the hydroxy terminated epoxide alcohol with the cyanuric chloride or monoalkoxy chlorotriazine at the interface between the phases, i.e., at the interface between the immiscible liquid phases or the liquid-solid phases of the reaction mixture.

An embodiment of the instant invention is a chlorotriazine compound having two epoxide groups obtained by reacting cyanuric chloride, an epoxy alcohol, and a base. The amount of base utilized is an amount effective to prepare sufficient anion of the alcohol to displace two chloride ions of the cyanuric chloride. It is believed an amount slightly in excess of the stoichiometric amount of base will facilitate completion of the reaction.

Another embodiment of the instant invention is a compound having only one epoxide group obtained by reacting a monoalkoxy chlorotriazine, an epoxy alcohol, and a base. The amount of base utilized is an amount effective to prepare sufficient anion to displace one chloro radical of the monoalkoxy chlorotriazine.

The reaction may be carried out batch wise or continuously, utilizing any apparatus desired, so long as means are provided for adding small increments of base. Moreover, reactants may be added in any way or order desired as long as the reaction takes place in the presence of sufficient water immiscible solvent to dissolve the reactants and the reaction product.

The reaction time is generally in the range of from about 15 minutes to about 8 hours, depending on the particular chloroepoxytriazine prepared. The reaction is conducted for a period of time sufficient to react cyanuric chloride or monoalkoxy chlorotriazine with two or one equivalents of hydroxy terminated epoxy compound, respectively.

The reaction product can be isolated by conventional means, such as solvent evaporation, precipitation with a non solvent such a methanol, ethanol, and water, and the like.

The chlorotriazine derivatives described herein are useful for making polymers having epoxytriazine groups at various places on the polymer chain. For example, nucleophile-containing polymers such as polyphenylene oxides and polycarbonates can be provided with a reactive epoxy group by reacting the chloroepoxytriazine with a hydroxy group on the polymer, e.g., in a toluene solution through displacement of the chlorine by the phenolic end group of the polymer.

Polymers having epoxy functional groups can be copolymerized with other nucleophile-containing polymers such as polyesters, polyamides and other polymers capable of reacting with an epoxy group.

The following examples illustrate the practice of the invention.

EXAMPLE I

Synthesis of 2-chloro-4,6-diglycidoxy-1,3,5-triazine

To a mechanically stirred solution of 220.8 g (1.2 mol) cyanuric chloride in 1500 ml chloroform, cooled to 0°–10° C., was added 266.4 g (3.6 mol) 2,3-epoxy-1-propanol in one portion. Aqueous sodium hydroxide (50% solution; 192 g) was added to the mixture dropwise with stirring over about 3 hr maintaining the reaction temperature below 10° C. and preferably around 0°–5° C. The reaction mixture was allowed to warm slowly to room temperature. The chloroform layer was washed with distilled water until neutral and dried over magnesium sulfate. The reaction product was found by nuclear magnetic resonance to be 2-chloro-4,6-diglycidoxy-1,3,5-triazine. Analysis showed about 95% (by weight) chlorodiglycidoxytriazine. The reaction mixture also was found to contain small amounts of triglycidoxytriazine and dichloro monoglycidoxytriazine.

This material was used to functionalize a polyphenylene oxide polymer.

EXAMPLE II

Synthesis of 2-chloro-4-butoxy-6-glycidoxy-1,3,5-triazine

To a magnetically stirred solution of 250 g (1.125 mol) butoxy dichlorotriazine in 757 ml chloroform, cooled to 0°–10° C., was added 250 g (3.375 mol) 2,3-epoxy-1-propanol in one portion. Aqueous sodium hydroxide (50% solution; 90 g) was added to the mixture dropwise with stirring over about 2 hr maintaining the reaction temperature below 10° C. and preferably around 0°–5° C. The reaction mixture was allowed to warm slowly to room temperature over 30 minutes. The chloroform layer was washed with distilled water until neutral and dried over magnesium sulfate. Proton nuclear magnetic resonance analysis indicated that the chloroform solution gave about 95% yield 2-butoxy-4-chloro-6-glycidoxy-1,3,5-triazine.

EXAMPLE III

Synthesis of 2-chloro-4-glycidoxy-6-(2,4,6-trimethylphenoxy)-1,3,5-triazine

To a mechanically stirred solution of 50 g (0.155 mol) 2,4-dichloro-6-(2,4,6-trimethylphenoxy)-1,3,5-triazine in 170 ml dichloromethane, cooled to 0° ∝ 10° C., was added 26.38 g (0.356 mol) 2,3-epoxy-1-propanol in one portion. Aqueous sodium hydroxide (50% solution; 14.26 g) was added to the mixture dropwise with stirring over about 25 minutes maintaining the reaction temperature between 0° and 10° C. and preferably around 0°–5° C. After stirring an additional 30 minutes, the reaction mixture was allowed to warm slowly to room temperature. The dichloromethane layer was washed with distilled water until neutral and dried over magnesium sulfate. The reaction product was found by proton nuclear magnetic resonance to be 2-chloro-4-glycidoxy-6-(2,4,6-trimethylphenoxy)-1,3,5-triazine.

The compounds of this invention undergo reaction with polyphenylene ethers to form intermediates capable of conversion of polyphenylene ether-polyester copolymers. Such intermediates and copolymers are disclosed and claimed in copending, commonly owned application Ser. No. 351,905, filed May 15, 1989.

What is claimed is:

1. A compound having the formula

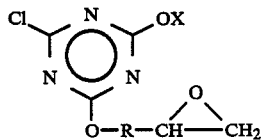

wherein R is an alkylene, cycloalkylene, aromatic hydrocarbon-substituted alkylene or divalent aromatic hydrocarbon radical having from 1 to about 18 carbon atoms and X is selected from the group consisting of alkyl, aromatic hydrocarbon and aromatic hydrocarbon-substituted alkyl radicals having from 1 to about 18 carbon atoms and

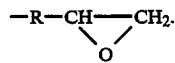

2. The compound according to claim 1, wherein R is alkylene having from 1 to about 6 carbon atoms.

3. The compound according to claim 2, where X is

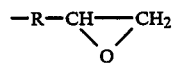

4. The compound according to claim 1, having the formula:

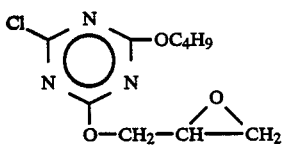

5. The compound according to claim 1, having the formula:

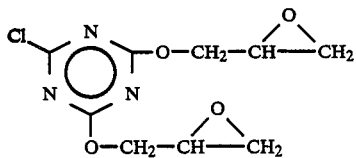

6. The compound according to claim 1, having the formula

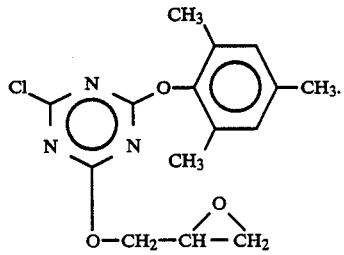

* * * * *